United States Patent
Stasch et al.

(10) Patent No.: US 7,115,599 B2
(45) Date of Patent: Oct. 3, 2006

(54) SULFONAMIDE-SUBSTITUTED PYRAZOLOPYRIDINE COMPOUNDS

(75) Inventors: Johannes-Peter Stasch, Solingen (DE); Achim Feurer, Wilhelmsfeld (DE); Stefan Weigand, Wuppertal (DE); Elke Stahl, Bergisch Gladbach (DE); Dietmar Flubacher, Freiburg (DE); Cristina Alonso-Alija, Haan (DE); Frank Wunder, Wuppertal (DE); Dieter Lang, Velbert (DE); Klaus Dembowsky, Boston, MA (US); Alexander Straub, Wuppertal (DE); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 219 days.

(21) Appl. No.: 10/432,572

(22) PCT Filed: Nov. 12, 2001

(86) PCT No.: PCT/EP01/13064

§ 371 (c)(1),
(2), (4) Date: Oct. 23, 2003

(87) PCT Pub. No.: WO02/42302

PCT Pub. Date: May 30, 2002

(65) Prior Publication Data

US 2004/0067937 A1    Apr. 8, 2004

(30) Foreign Application Priority Data

Nov. 22, 2000  (DE) ................................. 100 57 754

(51) Int. Cl.
*C07D 471/04*  (2006.01)
*A61K 31/437*  (2006.01)

(52) U.S. Cl. .................... 514/222.2; 514/256; 544/3; 544/326; 544/327; 544/328

(58) Field of Classification Search ................ 544/3, 544/326, 327, 328; 514/222.2, 256
See application file for complete search history.

(56) References Cited

U.S. PATENT DOCUMENTS

| 6,166,027 A | 12/2000 | Straub et al. ............... 514/283 |
| 6,180,656 B1 | 1/2001 | Fürstner et al. ............. 514/406 |
| 6,387,940 B1 | 5/2002 | Straub et al. ............... 514/403 |
| 6,410,740 B1 | 6/2002 | Straub et al. ............... 548/235 |
| 6,414,009 B1 | 7/2002 | Straub et al. ............... 514/403 |
| 6,451,805 B1 | 9/2002 | Straub et al. ............... 514/269 |
| 6,462,068 B1 | 10/2002 | Straub et al. ............... 514/403 |

FOREIGN PATENT DOCUMENTS

| WO | 9816223 | 4/1998 |
| WO | 9816507 | 4/1998 |
| WO | 9823619 | 6/1998 |
| WO | 0006567 | 2/2000 |
| WO | 0006568 | 2/2000 |
| WO | 0006569 | 2/2000 |
| WO | 0021954 | 4/2000 |

OTHER PUBLICATIONS

Fisker et al., PubMed Abstract (J Endocrinol Invest. 22(5 Suppl):89-93) 1999.*
Layzer, Degenerative Diseases of the Nervous System, Cecil Textbook of Medicine, 20th Edition, vol. 2, pp. 2050-2057, 1996.*
Damasio, Alzheimer's Disease and the related dementias, Cecil Textbook of Medicine, 20th Edition, vol. 2, pp. 1992-1996, 1996.*
Ko, et al., Blood 84, 4226-4233 (1994).
Mülsch, et al., Brit. J. Pharmacol., 120, 681-689 (1997).
Glass, et al., J. Biol. Chem., 252, 1279-1285 (1977).
Pettibone, et al., Eur. J. Pharmacol, 116, 307-312 (1985).
Yu et al., Brit. J. Pharmacol, 114, 1587-1594 (1995).

* cited by examiner

*Primary Examiner*—Deepak Rao

(57) ABSTRACT

This invention relates to compounds of the formula

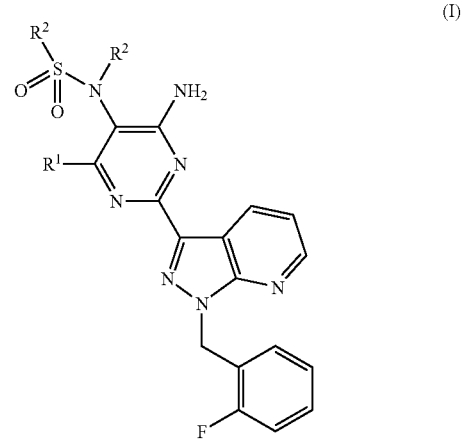

(I)

in which $R^1$, $R^2$, and $R^3$ are as defined in the claims, to a process for preparing such compounds, to pharmaceutical compositions containing such compounds, and to methods of using such compounds for treatment of hypertension and sexual dysfunction.

11 Claims, No Drawings

SULFONAMIDE-SUBSTITUTED PYRAZOLOPYRIDINE COMPOUNDS

This application is a 371 of PCT/EP01/13064 filed Nov. 12, 2001.

The present invention relates to novel chemical compounds which stimulate soluble guanylate cyclase, to the preparation thereof and to the use thereof as medicaments, in particular as medicaments for the treatment of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569 and WO 00/21954 describe pyrazolopyridine derivatives as stimulators of soluble guanylate cyclase. Also described inter alia in these patent applications are pyrazolopyridines having a pyrimidine residue in position 3. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrazolopyridine derivatives which act as stimulators of soluble guanylate cyclase but do not have the disadvantages, detailed above, of the compounds from the prior art.

This object is achieved according to the present invention by compounds as claimed in claim 1. These novel pyrazolopyridine derivatives are distinguished by having in position 3 a pyrimidine residue which has a particular substitution pattern, namely a sulfonamide residue in position 5 of the pyrimidine ring, and one or two amino groups in position 4 and, where appropriate, 6 of the pyrimidine rings.

The present invention specifically relates to compounds of the formula (I)

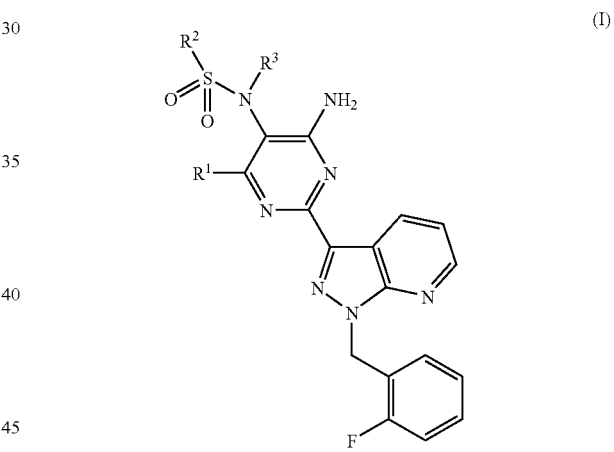

in which $R^1$ is H, Cl or $NH_2$;

$R^2$ and $R^3$ together with the heteroatoms to which they are bonded form a five-to seven-membered heterocycle which may be saturated or partially unsaturated, may optionally contain one or more other heteroatoms from the group of N, O, S, and may optionally be substituted;

and salts, isomers and hydrates thereof.

Preference is given according to the present invention to compounds of the formula (I) in which $R^1$ is H, Cl or $NH_2$;

$R^2$ and $R^3$ together with the heteroatoms to which they are bonded form a five- to seven-membered heterocycle which may be saturated or partially unsaturated, may optionally contain one or more other heteroatoms from the group of N, O, S;

and salts, isomers and hydrates thereof.

Particular preference is given in this connection to compounds of the formula (I) in which $R^1$ is H, Cl or $NH_2$;

$R^2$ and $R^3$ together with the heteroatoms to which they are bonded form a saturated five- to seven-membered heterocycle;

and salts, isomers and hydrates thereof.

The compounds of the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine or ethylenediamine.

The compounds of the invention may exist in stereoisomeric forms which either are related as image and mirror image (enantiomers) or which are not related as image and mirror image (diastereomers). The invention relates both to the enantiomers or diastereomers and to respective mixtures thereof. The racemic forms can, just like the diastereomers, be separated in a known manner, for example by chromatographic separation, into the stereoisomerically pure constituents. Double bonds present in the compounds of the invention may be in the cis or trans configuration (Z or E form).

In addition, certain compounds may exist in tautomeric forms. This is known to the skilled worker, and such compounds are likewise encompassed by the invention.

The compounds of the invention may additionally occur in the form of their hydrates, with the number of water molecules bound to the molecule depending on the particular compound of the invention.

Unless indicated otherwise, the substituents have for the purposes of the present invention in general the following meaning:

Alkyl is generally a straight-chain or branched hydrocarbon radical having 1 to 20 carbon atoms. Examples which may be mentioned are methyl, ethyl, propyl, isopropyl, butyl, isobutyl, pentyl, isohexyl, heptyl, isoheptyl, octyl and isooctyl, nonyl, decyl, dodeyl, eicosyl.

Alkylene is generally a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodeylene and eicosylene.

Alkenyl is generally a straight-chain of branched hydrocarbon radical having 2 to 20 carbon atoms and one or more, preferably having one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkynyl is generally a straight-chain or branched hydrocarbon radical having 2 to 20 carbon atoms and one or more, preferably having one or two, triple bonds. Examples which may be mentioned are ethynyl, 2-butynyl, 2-pentynyl and 2-hexynyl.

Acyl is generally straight-chain or branched lower alkyl having 1 to 9 carbon atoms which is linked via a carbonyl group. Examples which may be mentioned are: acetyl, ethylcarbonyl, propylcarbonyl, isopropylcarbonyl, butylcarbonyl and isobutylcarbonyl.

Alkoxy is generally a straight-chain or branched hydrocarbon radical having 1 to 14 carbon atoms which is linked via an oxygen atom. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy. The terms "alkoxy" and "alkyloxy" are used synonymously.

Alkoxyalkyl is generally an alkyl radical having up to 8 carbon atoms which is substituted by an alkoxy radical having up to 8 carbon atoms.

Alkoxycarbonyl can be represented for example by the formula

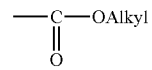

Alkyl in this case is generally a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl is generally a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Cycloalkoxy is for the purposes of the invention an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl is generally an aromatic radical having 6 to 10 carbon atoms. Preferred aryl radicals are phenyl and naphthyl.

Halogen is for the purposes of the invention fluorine, chlorine, bromine and iodine.

Heterocycle is for the purposes of the invention generally a saturated, unsaturated or aromatic 3- to 10-membered, for example 5- or 6-membered, heterocycle which may comprise up to 3 heteroatoms from the series S, N and/or O and, in the case of a nitrogen atom, may also be bonded via the latter. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3 triazolyl, thiazolyl, oxazolyl, imidazolyl, morpholinyl or piperidyl. Thiazolyl, furyl, oxazolyl, pyrazolyl, triazolyl, pyridyl, pyrimidinyl, pyridazinyl and tetrahydropyranyl are preferred. The term "heteroaryl" (or "hetaryl") stands for an aromatic heterocyclic radical.

The compounds of the invention of the formula (I) can be prepared by reacting the compound of the formula (II)

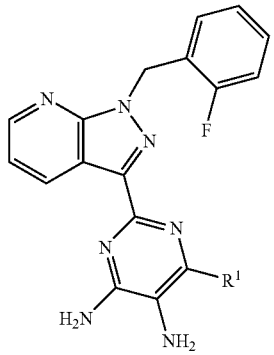

(II)

where R¹ is as defined above;
with a compound of the formula X-L-SO₂X
where
X is a leaving group which can be replaced by an amino group, such as, for example, halogen;
L is an alkanediyl group or an alkenediyl group having in each case 3 to 5 carbon atoms, where one or more carbon atoms may be replaced by one or more heteroatoms from the group of N, O, S, and where the group may optionally be substituted;
in the presence of an organic base at room temperature and subsequently reacting with a base in an organic solvent with heating.

The starting compound of the formula (IIa)

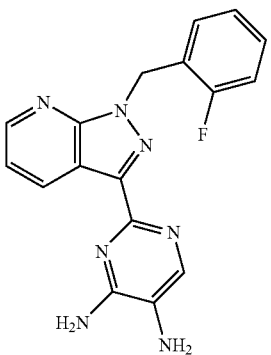

(IIa)

can be prepared by reacting the compound of the formula (III)

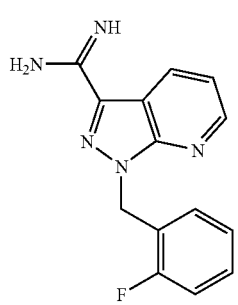

(III)

with the compound of the formula (IV)

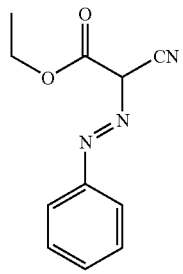

(IV)

in an organic solvent with heating to give a compound of the formula (V)

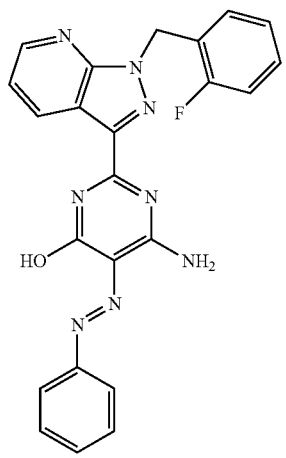

(V)

reacting with a reducing agent such as Raney nickel in the presence of hydrogen in an organic solvent with heating to give a compound of the formula (VI)

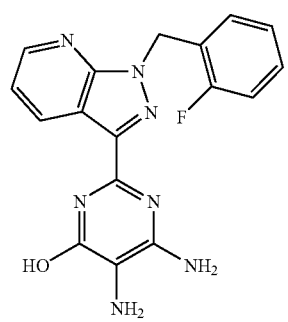

(VI)

and removal of the hydroxyl group by reaction with a chlorinating agent such as POCl₃ in the presence of an organic base with heating and subsequently reacting with ammonium formate in the presence of a catalyst in an organic solvent.

The starting compound of the formula (IIb)

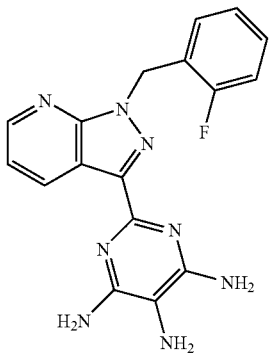
(IIb)

can be prepared by reacting the compound of the formula (III)

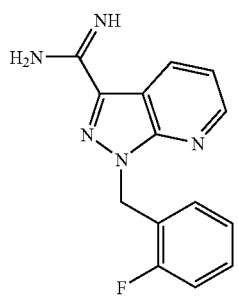
(III)

with the compound of the formula (VII)

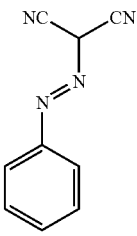
(VII)

in an organic solvent in the presence of a base with heating to give a compound of the formula (VIII)

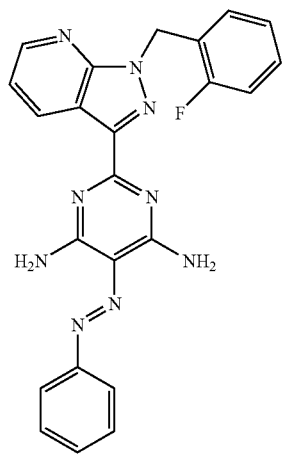
(VIII)

and reacting with a reducing agent such as Raney nickel in an organic solvent with heating.

The compound of the formula (III) can be prepared as shown in the following reaction scheme:

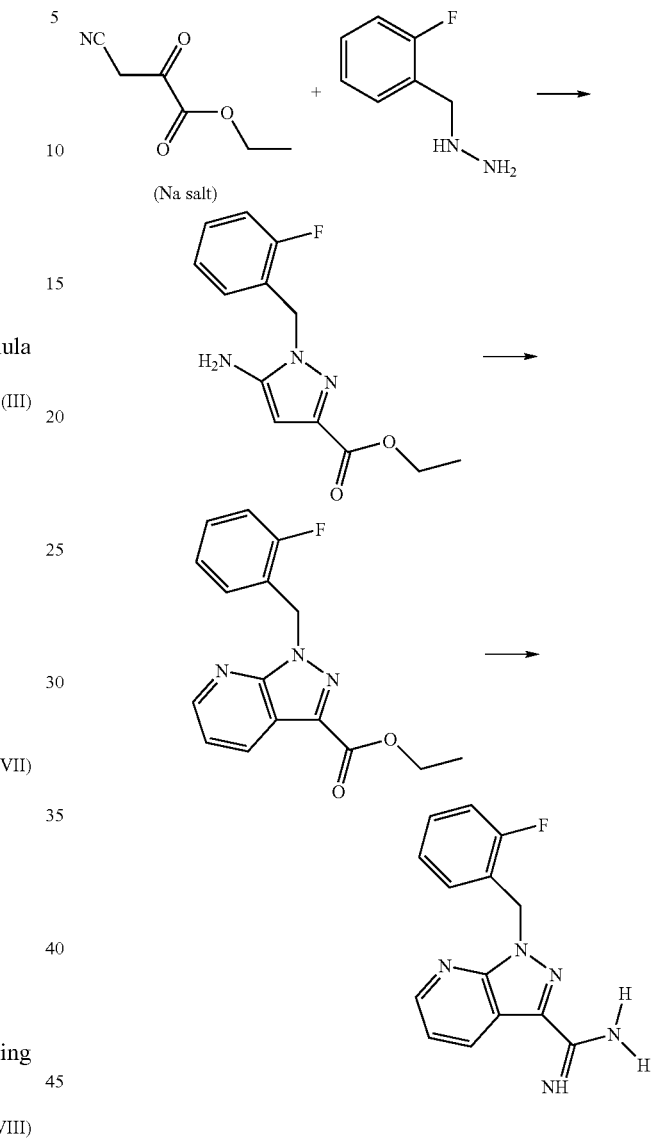

The compound of the formula (III) can be obtained in a multistage synthesis from the sodium salt of ethyl cyanopyruvate which is known from the literature (Borsche and Manteuffel, Liebigs. Ann. Chem. 1934, 512, 97). Reaction thereof with 2-fluoro-benzylhydrazine with heating under a protective gas atmosphere in an inert solvent such as dioxane results in ethyl 5-amino-1-(2-fluorobenzyl)pyrazole-3-carboxylate, which is cyclized by reaction with dimethylaminoacrolein in acidic medium under a protective gas atmosphere with heating to give the corresponding pyridine derivative. This pyridine derivative ethyl 1-(2-fluorobenzyl)-1H-pyrazolo[3,4-b]pyridine-3-carboxylate is converted by a multistage sequence consisting of conversion of the ester with ammonia into the corresponding amide, dehydration with a dehydrating agent such as trifluoroacetic anhydride to give the corresponding nitrile derivative, reaction of the nitrile derivative with sodium ethoxide and finally reaction with ammonium chloride into the compound of the formula (III).

The compound of the formula (IV) can be obtained from ethyl cyanoacetate and aniline by the method of Menon R., Purushothaman E., J. Indian Chem. Soc. 74 (1997), 123.

Reaction of the compound of the formula (III) with the compound of the formula (IV) to give the compound of the formula (V) can take place by reacting these reactants preferably in equimolar amounts, where appropriate in an organic solvent, for example an aromatic hydrocarbon, especially toluene, preferably under atmospheric pressure and stirring the reaction solution for several hours, for example 12 hours, at elevated temperature, for example 60–130° C., preferably with the solvent refluxing.

Reaction of the compound of the formula (V) to give the compound of the formula (VI) can take place by reaction with hydrogen in the presence of a catalyst conventionally employed for such reactions, such as, for example, Raney nickel, in an organic solvent conventionally employed for such reactions, such as, for example, dimethylformamide (DMF) (cf. also the statements concerning the synthesis of compound VIII), preferably by applying from 30 to 80 bar of hydrogen, in particular 50 to 70 bar of hydrogen, and stirring the reaction solution for several hours, for example 24 hours, at elevated temperature, for example 50–100° C., preferably at 50 to 80° C.

Removal of the hydroxyl group from the compound of the formula (VI) to obtain the compound of the formula (IIa) can preferably take place according to the invention by a two-stage reaction. In the first step according to the present invention the hydroxyl group is replaced by a halogen group, preferably a chlorine radical. This can take place by reacting the compound of the formula (VI) with a preferably equimolar amount of a halogenating agent, in particular a chlorinating agent such as, for example, $POCl_3$ in the presence of catalytic amounts of an organic base, for example an amine, preferably N,N-dimethylaniline, where appropriate in an organic solvent conventionally employed for such reactions, preferably under atmospheric pressure and stirring the reaction solution for several hours, for example 3 to 6 hours at elevated temperature, for example 60–130° C., preferably with the reaction solution refluxing. In the second step, the halogen radical such as the chlorine radical is then removed in a conventional way known to the skilled worker, for example by reaction with an excess, for example a seven- to fifteen-fold excess of ammonium formate in the presence of a catalyst conventionally employed for such reactions, such as, for example, Pd/C in an organic solvent conventionally employed for such reactions, such as, for example, an alcohol, preferably methanol, and stirring the reaction solution for several hours to several days, for example 1 to 3 days, at elevated temperature, for example 50–130° C., preferably with the reaction solution refluxing.

Synthesis of the compound of the formula (VII), phenylazomalononitrile, from aniline and malononitrile by diazotization is known from the literature (L. F. Cavalieri, J. F. Tanker, A. Bendich J. Am. Chem. Soc. 1949, 71, 533).

Reaction of the compound of the formula (IIb) with phenylazomalononitrile (compound of the formula (VII) takes place in the presence of a base. Bases which can be employed in this case are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, or alkaline earth metal carbonates such as calcium carbonate, or alkali metal or alkaline earth metal alcoholates such as sodium or potassium methanolate, sodium or potassium ethanolate or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium and hydrides thereof such as sodium hydride as bases. Sodium methanolate is preferred.

Solvents suitable in this case are inert organic solvents. These include ethers such as diethyl ether or tetrahydrofuran, DME, dioxane, alcohols such as methanol and ethanol, halohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane, or petroleum fractions, nitromethane, dimethylformamide, acetone, acetonitrile or hexamethylphosphoric triamide. It is likewise possible to employ mixtures of the solvents. Tetrahydrofuran, dimethylformamide, toluene, dioxane or dimethoxyethane is particularly preferred.

The reaction is carried out by heating at temperatures between 60° C. and 110° C. and under atmospheric pressure. The reaction mixture is allowed to react for about 5–24 hours, preferably 12 to 24 hours.

The compound of the formula (IIb) is then obtained by cleavage of the azo group. Reducing agents which can be used for this purpose are metals, in particular zinc, in the presence of mineral acids such as hydrochloric acid, $Na_2SO_4$, boranes or hydrogen in the presence of a catalyst. The use of hydrogen in the presence of Raney nickel is preferred according to the invention.

The solvents which can be employed are the aforementioned solvents. Dimethylformamide (DMF) is particularly preferred in this connection. The reaction is preferably carried out with heating, for example at 50–80° C., under a pressure of from 30 to 80 bar, preferably 50 to 70 bar, of hydrogen. The reactants are allowed to react for about 24 hours.

The compounds of the formula (II) obtained in this way can be converted into the compounds of the invention of the formula (I) by reaction with an equimolar amount or preferably an excess, for example a one- to five-fold excess, in particular a one- to three-fold excess, of a sulfonyl compound of the formula X-L-$SO_2$X, where X is a leaving group which can be replaced by an amino group, such as, for example, halogen, and L is an alkanediyl group or an alkenediyl group having in each case 3 to 5 carbon atoms, where one or more carbon atoms may be replaced by one or more heteroatoms from the group of N, O, S, and where the group may optionally be substituted. The reaction takes place in two steps. Firstly, the compounds of the formula (II) are reacted with an equimolar amount or preferably an excess, for example a one- to five-fold excess, in particular a one- to three-fold excess, of the sulfonyl compound of the formula X-L-$SO_2$X described above in the presence of a base such as an organic amine, preferably pyridine, preferably under atmospheric pressure and stirring the reaction solution for several hours, for example 12 hours, at room temperature. The sulfonyl compounds used in this case and described above can be purchased or be obtained in a manner known to the skilled worker. The intermediates obtained in this way are then dissolved in an organic solvent, an excess, for example a one- to ten-fold excess, in particular a three- to eight-fold excess, of a base is added, and the reaction solution is reacted preferably under atmospheric pressure and stirring for several hours, for example 12 hours, at elevated temperature for example 60–130° C., preferably, preferably 70–90° C. to give the compounds of the invention of the formula (I). Solvents suitable in this case are inert organic solvents. These include ethers such as diethyl ether or tetrahydrofuran, DME, dioxane, alcohols such as methanol and ethanol, halohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane, or petroleum fractions, nitromethane, dimethylformamide, acetone, acetonitrile or hexamethylphosphoric triamide. It is likewise possible to employ mixtures of the solvents. Dimethylformamide is particularly preferred. Bases which can be employed in this case are generally inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alcoholates such as sodium or potassium methanolate, sodium or potassium ethanolate or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium and hydrides thereof such as sodium hydride as bases. Potassium carbonate is preferred.

The compounds of the invention of the general formula (I) show a valuable range of pharmacological effects which could not have been predicted.

The compounds of the invention of the general formula (I) lead to vasorelaxation, inhibition of platelet aggregation and to a reduction in blood pressure and to an increase in coronary blood flow. These effects are mediated by direct stimulation of soluble guanylate cyclase and an intracellular increase in cGMP. In addition, the compounds of the invention of the general formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies, percutaneously transluminal angioplasties (PTAs), percutaneously transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, gastroparesis and incontinence.

The compounds of the invention of the general formula (I) are also suitable as active ingredients for controlling central nervous system diseases characterized by disturbances of the NO/cGMP system. They are suitable in particular for eliminating cognitive deficits, for improving learning and memory and for treating Alzheimer's disease. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The active ingredients are furthermore also suitable for controlling cerebral blood flow and thus represent effective agents for controlling migraine.

They are also suitable for the prophylaxis and control of the sequelae of cerebral infarctions such as stroke, cerebral ischemias and craniocerebral trauma. The compounds of the invention of the general formula (I) can likewise be employed for controlling states of pain.

In addition, the compounds of the invention have an antiinflammatory effect and can therefore be employed as antiinflammatory agents.

Furthermore the invention also encompasses the combination of the compounds of the invention of the general formula (I) with organic nitrates or NO donors.

Organic nitrates and NO donors for the purposes of the invention are generally substances which display their therapeutic effect via release of NO or NO species. Preference is given to sodium nitroprusside, nitroglycerine, isosorbide dinitrate, isosorbide mononitrate, molsidomine and SIN-1.

In addition, the invention also encompasses the combination with compounds which inhibit the breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compound of the invention, and the desired pharmacological effect is increased.

BIOLOGICAL INVESTIGATIONS

Vasorelaxant Effect In Vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increasing dosage in each case, and the height of the contraction is compared with the height of the contraction reached in the last preceding run. The concentration necessary to reduce the height of the control value by 50% ($IC_{50}$) is calculated from this. The standard application volume is 5 μl, and the DMSO content in the bath solution corresponds to 0.1%. The results are listed in Table 1 below:

TABLE 1

| Vasorelaxant effect in vitro | |
|---|---|
| Example No. | $IC_{50}$ [nM] |
| 1 | 290 |
| 3 | 350 |

Determination of the Liver Clearance In Vitro

Rats are anesthetized and heparinized, and the liver is perfused in situ through the portal vein. Primary rat hepatocytes are then obtained ex vivo from the liver using collagenase solution. $2 \cdot 10^6$ hepatocytes per ml were in each case incubated with the same concentration of the compound to be investigated at 37° C. The decrease in the substrate to be investigated over time was determined bioanalytically (HPLC/UV, HPLC/fluorescence or LC/MSMS) at in each case 5 timepoints in the period 0–15 min after the start of incubation. The clearance was calculated therefrom via the number of cells and weight of the liver.

Determination of the Plasma Clearance In Vivo

The substance to be investigated is administered intravenously as solution to rats via the tail vein. Blood is taken from the rats at fixed times and is heparinized, and plasma is obtained therefrom by conventional procedures. The substance is quantified in the plasma bioanalytically. The pharmacokinetic parameters are calculated from the plasma concentration/time courses found in this way by conventional non-compartmental methods used for this purpose.

The present invention includes pharmaceutical preparations which, besides non-toxic, inert pharmaceutically suitable carriers, comprise the compounds of the invention of the general formula (I), and process for the production of these preparations.

The active ingredient may also be present in microencapsulated form in one or more of the carriers indicated above.

The therapeutically effective compounds of the general formula (I) should be present in the abovementioned pharmaceutical preparations in a concentration of about 0.1 to 99.5, preferably of about 0.5 to 95, % by weight of the complete mixture.

The abovementioned pharmaceutical preparations may, apart from the compounds of the invention of the general formula (I), also comprise other active pharmaceutical ingredients.

It has generally proved advantageous both in human and in veterinary medicine to administer the active ingredient(s) of the invention in total amounts of about 0.01 to about 700, preferably 0.01 to 100, mg/kg of body weight per 24 hours, where appropriate in the form of a plurality of single doses, to achieve the desired results. A single dose comprises the active ingredient(s) of the invention preferably in amounts of about 0.1 to about 80, in particular 0.1 to 30, mg/kg of body weight.

The present invention is described in detail below by means of non-restrictive preferred examples. Unless indicated elsewhere, all quantitative data relate to percentages by weight.

EXAMPLES

Abbreviations

| | |
|---|---|
| RT: | room tempereature |
| EA: | ethyl acetate |
| MCPBA: | m-chloroperoxybenzoic acid |
| BABA: | n-butyl acetate/n-butanol/glacial acetic acid/phosphate buffer pH 6 (50:9:25.15; org. phase) |
| DMF: | N,N-dimethylformamide |

Mobile Phases for Thin-layer Chromatography

| | |
|---|---|
| T1 E1: | toluene-ethyl acetate (1:1) |
| T1 EtOH1: | toluene-methanol (1:1) |
| C1 E1: | cyclohexane-ethyl acetate (1:1) |
| C1 E2: | cyclohexane-ethyl acetate (1:2) |

Methods for Determining the HPLC Retention Times

Method A (HPLC-MS):

| | |
|---|---|
| Eluent: | A = CH$_3$CN  B = 0.6 g 30% HCl/1 H$_2$O |
| Flow rate: | 0.6 ml/min |
| Column oven: | 50° C. |
| Column: | Symmetry C18 2.1*150 mm |
| Gradient: | |

| Time (min) | % A | % B | Flow rate (ml/min) |
|---|---|---|---|
| 0 | 10 | 90 | 0.6 |
| 4 | 90 | 10 | 0.6 |
| 9 | 90 | 10 | 0.8 |

Method B (HPLC):

| | |
|---|---|
| Eluent: | A = 5 ml HClO$_4$/1 H$_2$O, B = CH$_3$CN |
| Flow rate: | 0.75 ml/min |
| L-R temperature: | 30.00° C. 29.99° C. |
| Column: | Kromasil C18 60*2 mm |
| Gradient: | |

| Time (min) | % A | % B |
|---|---|---|
| 0.50 | 98 | 2 |
| 4.50 | 10 | 90 |
| 6.50 | 10 | 90 |
| 6.70 | 98 | 2 |
| 7.50 | 98 | 2 |

Method C (HPLC):

| | |
|---|---|
| Eluent: | A = H$_3$PO$_4$ 0.01 mol/l, B = CH$_3$CN |
| Flow rate: | 0.75 ml/min |
| L-R temperature: | 30.01° C. 29.98° C. |
| Column: | Kromasil C18 60*2 mm |
| Gradient: | |

| Time (min) | % A | % B |
|---|---|---|
| 0.00 | 90 | 10 |
| 0.50 | 90 | 10 |
| 4.50 | 10 | 90 |
| 8.00 | 10 | 90 |
| 8.50 | 90 | 10 |
| 10.00 | 90 | 10 |

Method D (chiral HPLC):

| | |
|---|---|
| Eluent: | 50% isohexane, 50% ethanol |
| Flow rate: | 1.00 ml/min |
| Temperature: | 40° C. |
| Column: | 250*4.6 mm, packed with Chiralcel OD, 10 μm |

Method E (HPLC-MS):

| | |
|---|---|
| Eluent: | A = CH$_3$CN  B = 0.3 g 30% HCl/1 H$_2$O |
| Flow rate: | 0.9 ml/min |
| Column oven: | 50° C. |
| Column: | Symmetry C18 2.1*150 mm |
| Gradient: | |

| Time (min) | % A | % B | Flow rate (ml/min) |
|---|---|---|---|

-continued

Method E (HPLC-MS):

| 0 | 10 | 90 | 0.9 |
|---|----|----|----|
| 3 | 90 | 10 | 1.2 |
| 6 | 90 | 10 | 1.2 |

Starting Compounds

I. Synthesis of 1-2-fluorobenzyl)1H-pyrazolo[3,4-b]pyridine-3-carboxamidine

1A) Ethyl 5-amino-1-(2-fluorobenzyl)pyrazole-3-carboxylate

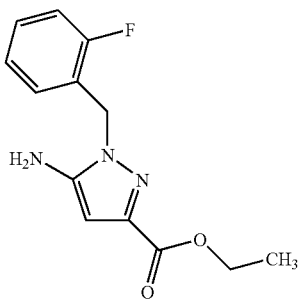

111.75 g (75 ml, 0.98 mol) of trifluoroacetic acid are added to 100 g (0.613 mol) of the sodium salt of ethyl cyanopyruvate (preparation in analogy to Borsche and Manteuffel, Liebigs Ann. 1934, 512, 97) in 2.5 l of dioxane under argon with efficient stirring at room temperature, and the mixture is stirred for 10 min, during which most of the precursor dissolves. Then 85.93 g (0.613 mol) of 2-fluorobenzyl-hydrazine are added, and the mixture is boiled overnight. After cooling, the sodium trifluoroacetate crystals which have separated out are filtered off with suction and washed with dioxane, and the crude solution is reacted further.

1B) Ethyl 1-(2-fluorobenzyl)-1H-pyrazolo[3,4-b]pyridine-3-carboxylate

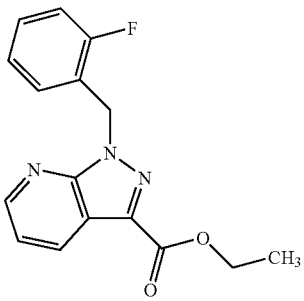

The solution obtained from 1A) is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is added to 2 l of water and extracted three times with 1 l of ethyl acetate each time. The combined organic phases are dried with magnesium sulfate and concentrated in a rotary evaporator. Chromatography is carried out on 2.5 kg of silica gel, eluting with a toluene/toluene-ethyl acetate=4:1 gradient. Yield: 91.6 g (49.9% of theory over two stages).

Melting point 85° C.

$R_f$ (SiO$_2$, T1E1): 0.83.

1C) 1-(2-Fluorobenzyl)-1H-pyrazolo[3,4-b]pyridine-3-carboxamide

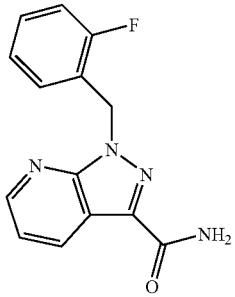

10.18 g (34 mmol) of the ester obtained in example 1B) are introduced into 150 ml of methanol saturated with ammonia at 0–10° C. Stirring at room temperature for two days is followed by concentration in vacuo.

$R_f$ (SiO$_2$, T1E1): 0.33.

1D) 3-Cyano-1-(2-fluorobenzyl)-1H-pyrazolo[3,4-b]pyridine

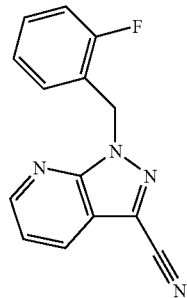

36.1 g (133 mmol) of 1-(2-fluorobenzyl)-1H-pyrazolo[3,4-b]pyridine-3-carboxamide from example 1C) are dissolved in 330 ml of THF, and 27 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. The mixture is then poured into 1 l of water and extracted three times with 0.5 l of ethyl acetate each time. The organic phase is washed with saturated sodium bicarbonate solution and with 1 N HCl, dried with MgSO4 and concentrated in a rotary evaporator.

Yield: 33.7 g (100% of theory)

Melting point 81° C.

$R_f$ (SiO$_2$, T1E1): 0.74.

1E) Methyl (2-fluorobenzyl)-1H-pyrazolo[3,4-b]pyridine-3-carboximidate

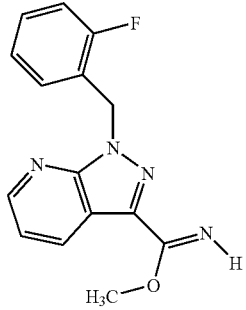

30.37 g (562 mmol) of sodium methoxide are dissolved in 1.5 l of methanol, and 36.45 g (144.5 mmol) of 3-cyano-1-

(2-fluorobenzyl)-1H-pyrazolo[3,4-b]pyridine (from example 1D) are added. The solution obtained after stirring at room temperature for 2 hours is employed directly for the next stage.

2F) 1-(2-Fluorobenzyl)-1H-pyrazolo[3,4-b]pyridine-3-carboxamidine

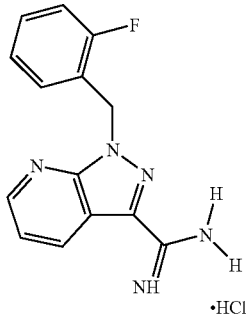

·HCl

The solution of methyl (2-fluorobenzyl)-1H-pyrazolo[3,4-b]pyridine-3-carboximidate in methanol obtained from example 1E) is mixed with 33.76 g (32.19 ml, 562 mmol) of glacial acetic acid and 9.28 g (173 mmol) of ammonium chloride and stirred under reflux overnight. The solvent is evaporated in vacuo, the residue is thoroughly triturated with acetone, and the precipitated solid is filtered off with suction.

$^1$H-NMR (d$_6$-DMSO, 200 MHz): δ=5.93 (s, 2H); 7.1–7.5 (m, 4H); 7.55 (dd, 1H); 8.12 (dd, 1H); 8.30 (dd, 1H); 9.5 (bs, 4H-exchangeable) ppm.

MS (EI): m/z=270.2 (M−HCl).

II. Synthesis of 6-amino-2-[1-(2-fluorobenzyl)-1H-pyrazolo[3,4-b]pyridin-3-yl]-5-[(E)-phenyldiazenyl]-4-pyrimidinol

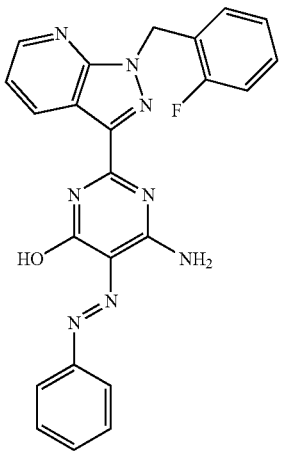

2.43 g (9.02 mmol) of 1-(2-fluorobenzyl)-1H-pyrazolo[3,4-b]pyridine-3-carboximidamide from example I and ethyl cyano[(E)-phenyldiazenyl]acetate (1.96 g, 9.02 mmol) were heated under reflux for 12 h. After cooling to room temperature, the precipitate which had separated out was filtered off and washed several times with toluene. Flash chromatography (CH$_2$Cl$_2$/ethyl acetate 50:1→EA) afforded the desired product.

Yield: 2.52 g (63%)

R$_f$: 0.72 (CH$_2$Cl$_2$/MeOH 20/1)

$^1$H-NMR: (300 MHz, D$_6$-DMSO), δ=5.87 (s, 2H, 2×CH$_2$O) 7.17 (t, 1H, Ar—H), 7.25 (d, 1H, Ar—H), 7.3–7.6 (m, 6H, Ar—H, NH$_2$), 7.80 (d, 2H, Ar—H), 8.75 (br. s, 2H, Ar—H), 9.05 (d, 1H), 10.23 (br. s, 1H), 12.1 (br. s, 1H).

LCMS: Ret. time: 3.94 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=441 ([M+H]$^+$), (ESI neg.), m/z=439 ([M−H]$^-$)

III. Synthesis of 5,6-diamino-2-[1-(2-fluorobenzyl)-1H-pyrazolo[3,4-b]-pyridin-3-yl]-4-pyrimidinol

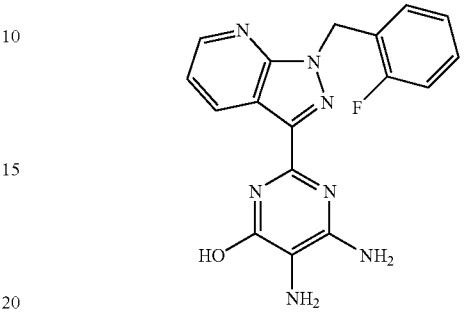

6-Amino-2-[1-(2-fluorobenzyl)-1H-pyrazolo[3,4-b]pyridin-3-yl]-5-[(E)-phenyldiazenyl]-4-pyrimidinol (2.52 g, 5.72 mmol) from example II and Raney Ni (50% in H$_2$O, 0.217 g) were dissolved in DMF and hydrogenated under 65 bar of H$_2$ at 62° C. for 22 h. Cooling was followed by taking up in DMF, heating to 100° C. and filtering off the catalyst. 10 ml of HCl (5 N) and H$_2$O (20 ml) were added to the mother liquor. After stirring at room temperature for 30 min, the precipitate which had separated out was filtered off and washed with H$_2$O.

Yield: 1.94 g (97%)

R$_f$: 0.10 (CH$_2$Cl$_2$/MeOH 10/1)

$^1$H-NMR: (300 MHz, D$_6$-DMSO), δ=5.78 (s, 2H, OCH$_2$), 5.90 (s, 2H, NH$_2$), 7.1–7.4 (m, 7H, Ar—H, NH$_2$), 8.64 (d, 1H, Ar—H), 8.85 (s, 1H, Ar—H), 11.7 (br. s, 1 H, OH).

LC-MS: Retention time: 2.74 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=352 ([M+H]$^+$), (ESI neg.), m/z=350 ([M−H]$^-$).

IV. Synthesis of 6-chloro-2-[1-(2-fluorobenzyl)-1H-pyrazolo[3,4-b]pyridin-3-yl]-4,5-pyrimidinediamine

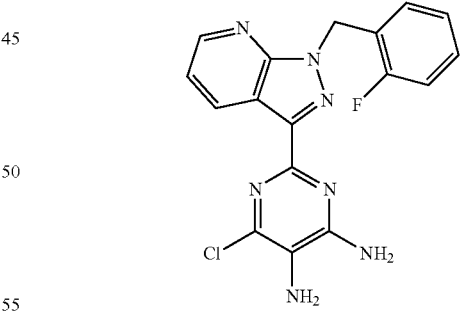

5,6-Diamino-2-[1-(2-fluorobenzyl)-1H-pyrazolo[3,4-b]pyridin-3-yl]-4-pyrimidinol (0.15 mg, 0.42 mmol) from example III was dissolved in POCl$_3$ (5 ml), and N,N-dimethylaniline (5.0 mg, 0.04 mmol), 0.1 equivalent) was added. After heating under reflux for 4 h, the excess reagent was removed in vacuo. The residue was taken up in ethyl acetate and washed with saturated aqueous NaHCO$_3$ solution, H$_2$O and saturated aqueous NaCl solution. The combined organic phases were concentrated and purified by flash chromatography (CH$_2$Cl$_2$:MeOH 40:1).

Yield: 0.12 g (77%)

R$_f$: 0.60 (CH$_2$Cl$_2$/MeOH 10:1)

LCMS: Retention time: 3.70 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=370 ([M+H]$^+$), (ESI neg.), m/z=368 ([M–H]$^-$).

V. Synthesis of 2-[1-(2-fluorobenzyl)-1H-pyrazolo[3,4-b]pyridin-3-yl]-4,5-pyrimidinediamine

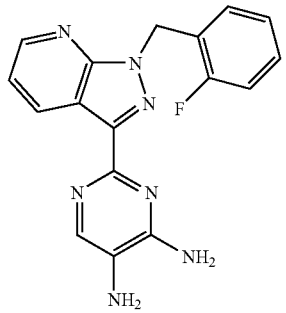

6-Chloro-2-[1-(2-fluorobenzyl)-1H-pyrazolo[3,4-b]pyridin-3-yl]-4,5-pyrimidinediamine (74 mg, 0.20 mmol) from example V was dissolved in MeOH (4 ml), and Pd/C (10%, 20 mg) and ammonium formate (126 mg, 2.00 mmol, 10 equivalents) were added. The mixture was heated under reflux for 2 days and then allowed to cool to room temperature before the catalyst was filtered off. Purification took place by preparative HPLC (column: Cromsil 120 ODS, C-18, 10 μm, 250×30 mm, flow rate 50 ml/min, room temperature, gradient: water acetonitrile at 0 min: 90:10, at 28 min 5:95) afforded the desired product.

Yield: 0.054 g (80%)

R$_f$: 0.10 (CH$_2$Cl$_2$/MeOH 20:1)

$^1$H-NMR: (300 MHz, D$_6$-DMSO), δ=5.90 (s, 2H, OCH$_2$), 7.1–7.6 (m, 6H, Ar—H), 8.75 (d, 1H, Ar—H), 8.98 (d, 1H, Ar—H).

LCMS: Ret. time: 2.66 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=336 ([M+H]$^+$), (ESI neg.), m/z=334 ([M–H]$^-$).

VI. Synthesis of 2-[1-(2-fluorobenzyl)-1H-pyrazolo[3,4-b]pyridin-3-yl]-5-[(E)-phenyldiazenyl]-4,6-pyrimidinediamine

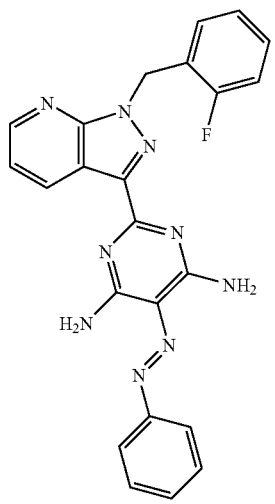

3.87 g of sodium methanolate and then 12.2 g (71.7 mmol) of phenylazomalonitrile (L. F. Cavalieri, J. F. Tanker, A. Bendich J. Am. Chem. Soc. 1949, 71, 533) are added to a stirred solution of 21.92 g (71.1 mmol) of 1-(2-fluorobenzyl)1H-pyrazolo[3,4-b]pyridine-3-carboxamidine in toluene from example I. The mixture is stirred at 110° C. overnight and allowed to cool. The solid which precipitates thereby is filtered off with suction and washed with ethanol. Drying results in 23 g (73% of theory) of the desired compound.

R$_f$: 0.50 (toluene/EA 1:1)

$^1$H-NMR: (300 MHz, D$_6$-DMSO), δ=5.88 (s, 2H, OCH$_2$), 7.1–7.5 (m, 7H, Ar—H), 7.87 (br. s, 2H, NH$_2$), 7.96 (s, 2H, Ar—H), 8.00 (s, 1H, Ar—H), 8.03 (s, 1H, Ar—H), 8.48 (br. s, 2H, NH$_2$), 8.65 (d, 1H, Ar—H), 9.20 (d, 1H, Ar—H).

MS: (ESI pos.), m/z=440 ([M+H]$^+$).

VII. Synthesis of 2-[1-(2-fluorobenzyl)-1H-pyrazolo[3,4-b]pyridin-3-yl]-4,5,6-pyrimidinetriamine trihydrochloride

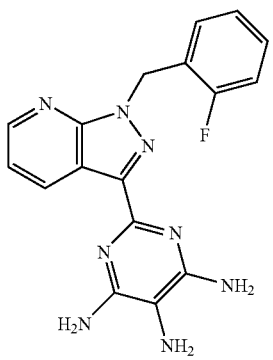

5 g (11.38 mmol) of 2-[1-(2-fluorobenzyl)-1H-pyrazolo[3,4-b]pyridin-3-yl]-5-[(E)phenyldiazenyl]-4,6-pyrimidinediamine from example VI are hydrogenated with 800 mg of 50 percent Raney nickel in water in 60 ml of DMF under a pressure of 65 bar of hydrogen and at 62° C. for 22 hours. The catalyst is filtered off with suction through kieselguhr, and the solution is evaporated in vacuo and stirred with 5 N HCl. The yellow-brown precipitate which has separated out is filtered off with suction and dried. 3.1 g (59.3% of theory) of the desired compound are obtained. The free base is obtained by shaking with dilute NaHCO$_3$ solution and extracted with ethyl acetate. The solid which is insoluble in both phases is filtered off with suction. The ethyl acetate phase also contains small amounts of free base.

R$_f$: 0.18 (EA)

$^1$H-NMR: (300 MHz, D$_6$-DMSO), δ=4.45 (br. s, 6H, NH$_2$), 5.92 (s, 2H, OCH$_2$), 7.1–7.6 (m, 5H, Ar—H), 8.76 (d, 2H, Ar—H), 8.98 (d, 1H, Ar—H).

VIII. 6-Amino-5-(1,1-dioxido-2-isothiazolidinyl)-2-[1-(2-fluorobenzyl)-1H-pyrazolo[3,4-b]pyridin-3-yl]-4-pyrimidinol

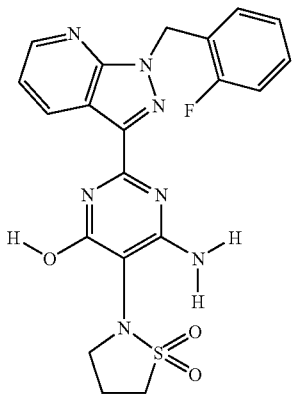

5,6-Diamino-2-[1-(2-fluorobenzyl)-1H-pyrazolo[3,4-b]pyridin-3-yl]-4-pyrimidinol (0.25 g, 0.71 mmol) from example III was introduced into pyridine (2.5 ml), and 3-chloropropanesulfonyl chloride (0.19 g, 1.1 mmol, 1.5 equivalents) was added. After 12 h at room temperature, the mixture was concentrated in vacuo and dissolved in DMF (2.5 ml). After addition of $K_2CO_3$ (0.69 g, 5.0 mmol, 7 equivalents), the mixture was stirred at 40° C. for 20 h. It was taken up in ethyl acetate and $H_2O$ and extracted several times with ethyl acetate. The combined organic phases were dried over $Na_2SO_4$ and concentrated in vacuo. The crystals obtained in this way were stirred with $CH_3CN$, filtered off with suction and dried in vacuo.

Yield: 0.128 g (39%)

$^1$H-NMR: (300 MHz, $D_6$-DMSO), δ=2.43 (br. s, 2H, $CH_2$), 3.29 (br. s, 2H, $CH_2$), 3.60 (br. d, 2H, $CH_2$), 5.82 (s, $CH_2O$), 6.8 (br. s, 2H, $NH_2$), 7.1–7.5 (m, 5H, Ar—H), 8.45 (s, 1H, Ar—H), 8.69 (d, 1H, Ar—H), 8.90 (d, 1H, Ar—H), 11.93 (s, 1H, OH).

LCMS: Retention time: 3.36 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90));

MS: (ESI pos.), m/z=456 ([M+H]$^+$), (ESI neg.), m/z=4.54 ([M+H]$^-$)

EXAMPLES 1. 6-Chloro-5-(1,1-dioxido-2-isothiazolidinyl)-2-[1-(2-fluorobenzyl)-1H-pyrazolo[3,4-b]pyridin-3-yl]-4-pyrimidinediamine

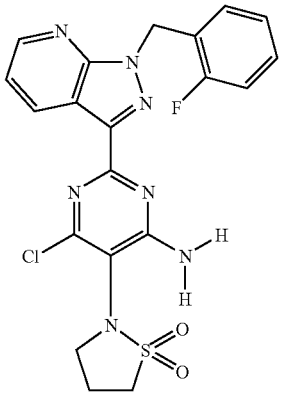

6-Amino-5-(1,1-dioxido-2-isothiazolidinyl)-2-[1-(2-fluorobenzyl)-1H-pyrazolo[3,4-b]pyridin-3-yl]-4-pyrimidinol (0.080 g, 0.18 mmol) from example VIII and dichlorophenylphosphine oxide (2.0 ml) were stirred at 160° C. for 2 h. Cooling was followed by hydrolysis with ice-water and purification of the crude product by preparative HPLC (column: Cromsil 120 ODS, C-18, 10 μm, 250×30 mm, flow rate 50 ml/min, room temp., gradient: water acetonitrile at 0 min: 90:10, at 28 min 5:95).

Yield: 0.050 g (60%)

$^1$H-NMR: (300 MHz, $D_6$-DMSO), δ=2.55 (t, 2H, $CH_2$), partly overlapped by DMSO, 3.36 (t, 2H, $CH_2$), partly overlapped by $H_2O$, 3.64 (tt, 2H, $CH_2$), 5.84 (s, $CH_2O$), 7.1–7.5 (m, 5H, Ar—H), 7.9 (br. s, 2H, $NH_2$), 8.66 (dd, 1H, Ar—H), 8.91 (d, 1H, Ar—H).

LCMS: Ret. time: 3.90 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=474 ([M+H]$^+$), (ESI neg.), m/z=472 ([M+H]$^-$)

2. 5-(1,1-Dioxido-2-isothiazolidinyl)-2-[1-(2-fluorobenzyl)-1H-pyrazolo[3,4-b]pyridin-3-yl]-4-pyrimidinediamine

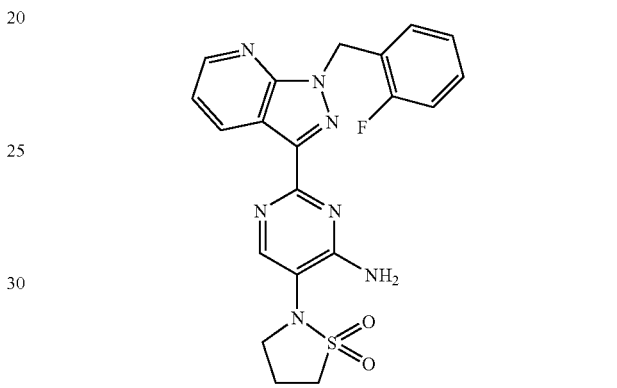

3-Chloropropanesulfonyl chloride (79 mg, 0.45 mmol, 3 equivalents) was added to 2-[1-(2-fluorobenzyl)-1H-pyrazolo[3,4-b]pyridin-3-yl]-4,5-pyrimidinediamine (50 mg, 0.15 mmol) from example V in pyridine (1.3 ml) at room temperature. The mixture was stirred at room temperature for 12 h and further 3-chloropropanesulfonyl chloride (39 mg, 0.23 mmol, 1.5 equivalents) was added. After 6 h, excess reagent was removed in vacuo, and the product was purified by flash chromatography ($CH_2Cl_2$:MeOH 20:1). The intermediate obtained in this way was taken up in DMF (1 ml) and, after addition of $K_2CO_3$ (144 mg, 1.04 mmol, 7 equivalents), heated at 80° C. for 12 h. DMF was then removed in vacuo, and the product was purified by flash chromatography ($CH_2Cl_2$:MeOH 20:1).

Yield: 0.021 g (32%)

$R_f$: 0.45 ($CH_2Cl_2$/MeOH 20:1)

$^1$H-NMR: (300 MHz, $D_6$-DMSO), δ=2.60 (tt, 2H, $CH_2$), 3.41 (t, 2H, $CH_2$), 3.75 (t, 2H, $CH_2$), 5.70 (br. s, 2H, $NH_2$), 5.94 (s, $CH_2O$), 6.9–7.4 (m, 5H, Ar—H, $NH_2$), 8.45 (s, 1H, Ar—H), 8.60 (d, 1H, Ar—H), 8.91 (d, 1H, Ar—H).

LCMS: Ret. time: 3.10 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=440 ([M+H]$^+$), (ESI neg.), m/z=438 ([M+H]$^-$).

Alternatively, 5-(1,1-dioxido-2-isothiazolidinyl)-2-[1-(2-fluorobenzyl)-1H-pyrazolo[3,4-b]pyridin-3-yl]-4-pyrimidinylamine (example 2) was prepared from 6-chloro-5(1,1-dioxido-2-isothiazolidinyl)-2-[1-(2-fluorobenzyl)-1H-pyrazolo[3,4-b]pyridin-3yl]-4-pyrimidineamine (0.040 mg, 0.084 mmol) from example 1, which was dissolved in MeOH (4 ml) and to which Pd/C (10%, 0.009 g) and ammonium formate (0.053 mg, 0.84 mmol, 10 equivalents) were added. The mixture was heated under reflux for 2 days and then allowed to cool to room temperature, before the catalyst was filtered off. The crude product was concentrated in vacuo.

Yield: 0.007 g (19%).

The spectroscopic data were identical to the product prepared by the route described previously.

3. 5-(1,1-Dioxido-2-isothiazolidinyl)-2-[1-(2-fluorobenzyl)-1H-pyrazolo[3,4-b]pyridin-3-yl]-4,6-pyrimidineamine

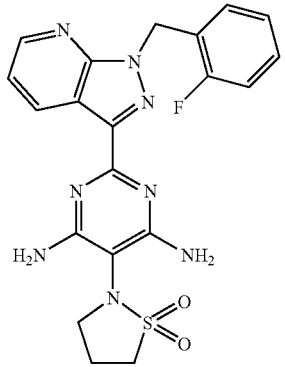

2-[1-(2-Fluorobenzyl)-1H-pyrazolo[3,4-b]pyridin-3-yl]-4,5,6-pyrimidinetriamine (0.30 g, 0.86 mmol) from example VII was dissolved in pyridine (2 ml) at room temperature, and 3-chloropropanesulfonyl chloride (0.23 g, 1.3 mmol, 1.5 equivalents) was added. After stirring at room temperature for 12 h, the solvent was removed in a rotary evaporator. The crude product obtained in this way was dissolved in DMF (1 ml), and $K_2CO_3$ (0.83 g, 6.0 mmol, 7 equivalents) was added. The mixture was stirred at 80° C. for 12 h. The crude mixture was purified by preparative HPLC (column: Cromsil 120 ODS, C-18, 10 μm, 250×30 mm, flow rate 50 ml/min, room temp., gradient: water acetonitrile at 0 min: 90:10, at 28 min 5:95).

Yield: 0.22 g (55%)

$R_f$: 0.25 ($CH_2Cl_2$/MeOH 20:1)

$^1$H-NMR: (300 MHz, $D_6$-DMSO), δ=2.45 (tt, 2H, $CH_2$, partly overlapped by DMSO), 3.46 (t, 2H, $CH_2$), partly overlapped by 3.50 (t, 2H, $CH_2$), 5.81 (s, $CH_2O$), 6.6 (br. s, 4H, 2×$NH_2$), 7.1–7.4 (m, 5H, Ar—H), 8.62 ($m_c$, 1H, Ar—H), 9.03 (d, 1H, Ar—H).

LCMS: Ret. time: 2.80 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.) m/z=455 ([M+H]$^+$), (ESI neg.), m/z=499 ([M+H, +HCOOH]$^-$).

4. 5-(1,1-Dioxido-1,2-thiazinan-2-yl)-2-[1-(2-fluorobenzyl)-1H-pyrazolo[3,4-b]pyridin-3-yl]-4,6-pyrimidineamine

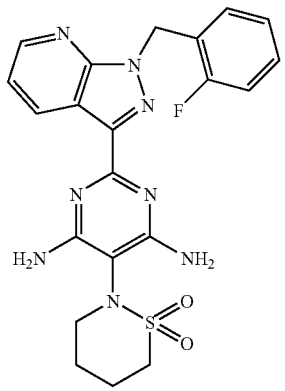

2-[1-(2-Fluorobenzyl)-1H-pyrazolo[3,4-b]pyridin-3-yl]-4,5,6-pyrimidinetriamine (0.080 g, 0.23 mmol) from example VII was dissolved in pyridine (5 ml) at room temperature, and 4-chlorobutanesulfonyl chloride (0.065 g, 0.34 mmol, 1.5 equivalents; preparation from tetrahydrothiophene as described by Runge et al., J. Prakt. Chem. 1955, 279, 288) was added. After stirring at room temperature for 12 h, the solvent was removed in a rotary evaporator. The crude product obtained in this way was dissolved in DMF (1 ml), and $K_2CO_3$ (0.22 g, 1.6 mmol, 7 equivalents) was added. The mixture was stirred at 80° C. for 12 h. The crude mixture was purified by preparative HPLC (column: Cromsil 120 ODS, C-18, 10 μm, 250×30 mm, flow rate 50 ml/min, room temp., gradient: water acetonitrile at 0 min: 90:10, at 28 min 5:95).

Yield: 0.022 g (19%)

$R_f$: 0.25 ($CH_2Cl_2$/MeOH 20:1)

$^1$H-NMR: (300 MHz, $D_6$-DMSO), δ=1.90 ($m_c$, 2H, $CH_2$), 2.15 ($m_c$, 2H, $CH_2$), 3.48 ($m_c$, 4H, 2×$CH_2$), 5.80 (s, $CH_2O$), 6.48 (br. s, 4H, 2×$NH_2$), 7.1–7.4 (m, 5H, Ar—H), 8.61 ($m_c$, 1H, Ar—H), 9.05 (d, 1H, Ar—H).

LCMS: Retention time: 2.90 min (column: Symmetry, C-18, 3.5 μm, 50×2.1 mm, flow rate 0.5 ml/min, 40° C., gradient: water (+0.1% formic acid):acetonitrile (+0.1% formic acid) at 0 min: 90:10, at 6.0 min 10:90)); MS: (ESI pos.), m/z=469 ([M+H]$^+$).

The invention claimed is:

1. A compound of the formula (I)

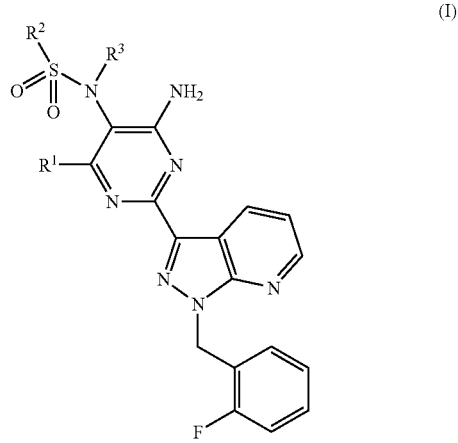

in which $R^1$ is H, Cl or $NH_2$; and $R^2$ and $R^3$ together with the heteroatoms to which they are bonded form a five- to seven-membered heterocycle which may be saturated or partially unsaturated, may optionally contain one or more other heteroatoms from the group of N, O, S, and may optionally be substituted;

or a salt, stereoisomer or hydrates thereof.

2. A compound as claimed in claim 1, in which $R^1$ is H, Cl or $NH_2$; and $R^2$ and $R^3$ together with the heteroatoms to which they are bonded form a five- to seven-membered heterocycle which may be saturated or partially unsaturated, and may optionally contain one or more other heteroatoms chosen from the group of N, O, S;

or a salt, stereoisomer or hydrates thereof.

3. A compound as claimed in claim 1, in which $R^1$ is H, Cl or $NH_2$; and

R² and R³ together with the heteroatoms to which they are bonded form a saturated five- to seven-membered heterocycle;
or a salt, stereoisomer or hydrates thereof.

4. A process for preparing compounds of the formula I,

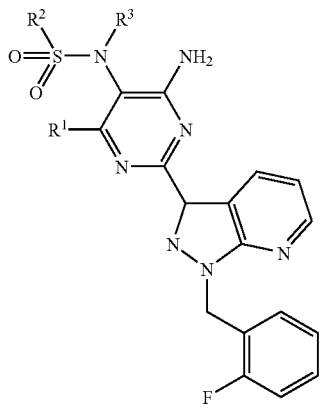
(I)

wherein R¹, R², and R³ are as defined above in claim 1, comprising reaction of a compound of the formula (II)

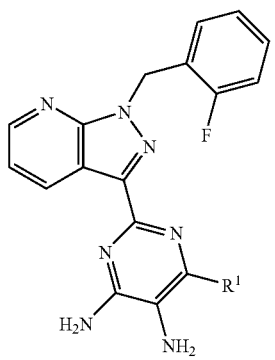
(II)

where R¹ is as definded above in claim 1;
with a compound of the formula X-L-SO₂X where
X is a leaving group which can be replaced by an amino group,
L is an alkanediyl group or an alkenediyl group having in each case 3 to 5 carbon atoms, where one or more carbon atoms may be replaced by one or more heteroatoms chosen from N, O, and S, and where the group may optionally be substituted;
in the presence of an organic base at room temperature and subsequent reaction with a base in an organic solvent with heating.

5. The process of claim 4 wherein in the formula X-L-SO₂X, the group X is Cl.

6. A pharmaceutical composition comprising at least one compound of the formula (I) as defined in claim 1.

7. A pharmaceutical composition comprising at least one compound of the formula (I) as defined in claim 1 in combination with at least one organic nitrate or NO donor.

8. A pharmaceutical composition comprising at least one compound of the formula (I) as defined in claim 1 in combination with at least one compound which inhibits the breakdown of cyclic guanosine monophosphate (cGMP).

9. A method for the treatment of hypertension comprising administering an effective amount of a compound of formula (I) as defined in claim 1.

10. A method for the treatment of sexual dysfunction comprising administering an effective amount of a compound of formula (I) as defined in claim 1.

11. The method as defined in claim 9 or 10, where the compound of the general formula (I) as claimed in claim 1 is employed in combination with at least one organic nitrate or NO donor or in combination with at least one compound which inhibits the breakdown of cyclic guanosine monophosphate (cGMP).

* * * * *